United States Patent [19]

Bristol et al.

[11] Patent Number: 4,464,372

[45] Date of Patent: Aug. 7, 1984

[54] IMIDAZO[1,2-B]PYRIDAZINES

[75] Inventors: James A. Bristol, Ann Arbor, Mich.; Raymond G. Lovey, West Caldwell, N.J.

[73] Assignee: Schering Corporation, Kenilworth, N.J.

[21] Appl. No.: 408,358

[22] Filed: Aug. 16, 1982

[51] Int. Cl.³ ............................................. C01G 56/00
[52] U.S. Cl. ..................................... 424/250; 544/236
[58] Field of Search ................ 544/236; 260/239 AR; 424/250; 542/431

[56] References Cited

U.S. PATENT DOCUMENTS

| | | | |
|---|---|---|---|
| 3,711,613 | 1/1973 | Tomcufcik et al. | 424/250 |
| 4,060,614 | 11/1977 | Adam | 424/250 |
| 4,358,453 | 11/1982 | Bristol et al. | |
| 4,358,454 | 11/1982 | Bristol et al. | |

FOREIGN PATENT DOCUMENTS 2208830  8/1972  Fed. Rep. of Germany ...... 544/236

Primary Examiner—Donald G. Daus
Assistant Examiner—William A. Teoli, Jr.
Attorney, Agent, or Firm—Gerald S. Rosen

[57] ABSTRACT

There are disclosed herein certain substituted imidazo[1,2-b]pyridazine compounds which are useful in the treatment of peptic ulcer diseases.

15 Claims, No Drawings

IMIDAZO[1,2-B]PYRIDAZINES

SUMMARY OF THE INVENTION

This invention relates to certain substituted imidazo[1,2-b]pyridazine compounds, pharmaceutical compositions thereof, novel processes and intermediates for making said compounds, and methods of treating peptic ulcer disease utilizing said compounds.

More particularly, this invention relates to imidazo[1,2-b]pyridazine compounds represented by the following structural formulas I and II

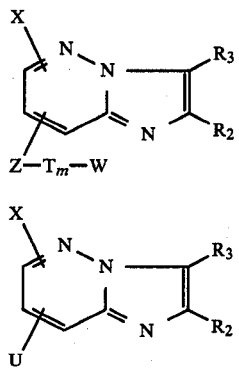

the 2,3-dihydro, the 5,6,7,8 tetrahydro and the perhydro derivatives thereof, and the pharmaceutically acceptable salts thereof, wherein: U represents:

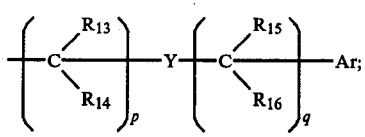

$R_2$ and $R_3$ each independently represent hydrogen, lower alkyl, trifluoromethyl, B—$CF_3$, Ar, B—Ar, halogen, B-halogen, —$OR_7$, B—$OR_8$, B—$SR_6$, —$S(O)_nR_7$, B—$S(O)_n$lower alkyl (wherein n is zero, one or two)

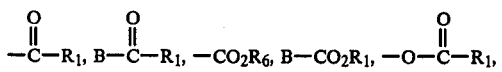

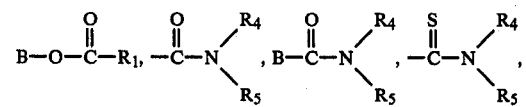

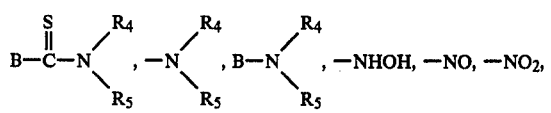

B—$NO_2$, —CN, B—CN, —NC, B—NC, —SCN, —$S(O)_nCF_3$,

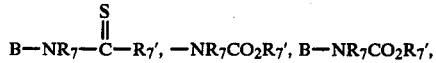

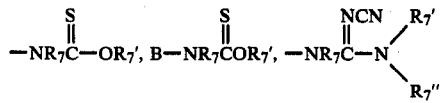

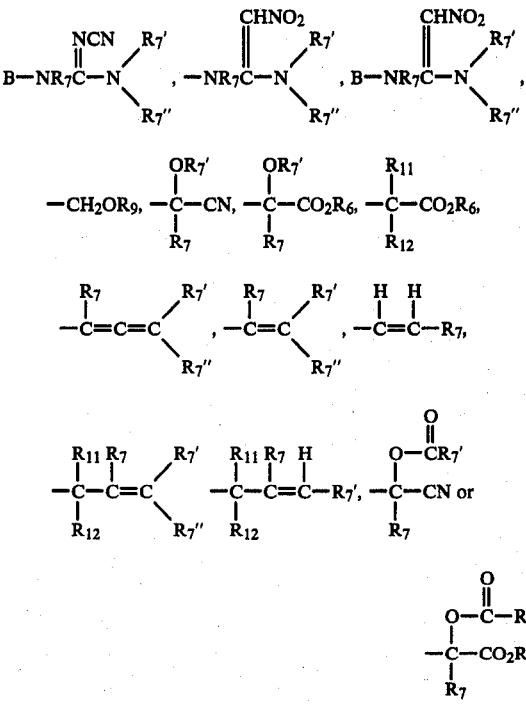

or a straight- or branched-chain alkenyl or alkynyl group having 2 to 6 bridging carbon atoms, aryl-substituted derivatives thereof or taken together are a cyclic alkyl of 3 to 6 bridging carbon atoms;

X represents hydrogen, lower alkyl, halogen, hydroxy, lower alkoxy, trifluoromethyl, —$COOR_6$,

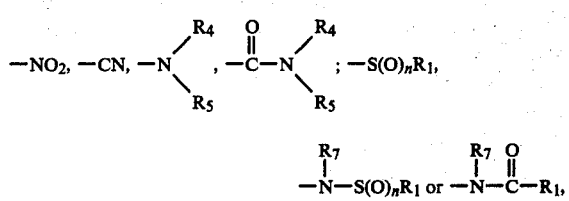

wherein n is zero, one or two with the proviso that when $R_1$ represents

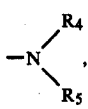

n represents two;

Z represents —O—, —S—, —SO—, —$SO_2$—, —$NR_6$—, or a bond connecting T to the 6- or 7-position of the imidazo[1,2-b]pyridazine nucleus;

B represents a straight- or branched-chain lower alkylene moiety;

T represents a straight-or branched-chain lower alkylene moiety and, (a) when Z is a bond connecting T and the imidazo[1,2-b]pyridazine nucleus, T represents the —$OR_7$ derivatives of said imidazo[1,2-b]pyridazine or the α(β)- or the β(γ)-unsaturated derivatives of said imidazo[1,2-b]pyridazine; or (b) when Z is —O—, T also represents the allylene (—$CH_2$—CH=CH—) derivatives of said imidazo[1,2-b]pyridazine;

When T is indicated to be such unsaturated derivative, e.g. ethenylene or propenylene, it is intended to mean the trans-isomer, the cis-isomer, or mixtures thereof, although for convenience the formulas are depicted herein as mixtures. Generally, either the trans- or cis- is the more active isomer.

m is zero to 10 with proviso that when W is Ar, m is not zero and the number of bridging carbons between Z and W is no greater than 5.

W represents hydrogen when T is allylene; or Ar, wherein Ar represents phenyl, pyridyl, thienyl, imidazolyl, furanyl or X'-, Y'-, and Z'-substituted-phenyl wherein each of X'-, Y'- and Z'-independently is as hereinabove defined for X; and when m is 1 to 3, W represents alkenyl, alkynyl, $Z^1R_6$ or $Z^1COR_6$, wherein $Z_1$ is —O—, —S—, —SO—, —SO$_2$— or —NR$_6$—;

Y represents —O—, —S—, —SO—, —SO$_2$— or —NR$_6$—; wherein in the above definitions:

$R_1$ represents Ar, lower alkyl,

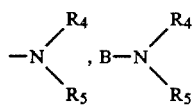

or Ar-lower alkyl;

$R_4$ and $R_5$ each independently represents hydrogen, lower alkyl, Ar, Ar-lower alkyl, lower alkoxy lower alkyl, trifluoromethyl lower alkyl, or when taken together with the nitrogen atoms to which they are attached represent a 4- to 7-membered cyclic amino or a morpholino group;

$R_6$ represents hydrogen, $C_1$- to $C_{12}$-alkyl, aryl or an arylalkyl group having up to 12 carbon atoms;

$R_7$, $R_7'$ and $R_7''$ each independently represents hydrogen or lower alkyl;

$R_8$ represents hydrogen, lower alkyl, lower alkoxy lower alkyl, trifluoromethyl lower alkyl, Ar-lower alkyl, or Ar;

$R_9$ represents

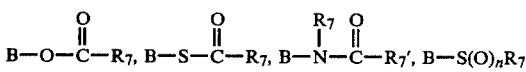

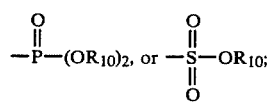

$R_{10}$ represents hydrogen, alkali metal or lower alkyl;

$R_{11}$ and $R_{12}$ each independently represents hydrogen or lower alkyl or together represent oxygen;

$R_{13}$ and $R_{14}$ each independently represents hydrogen, alkyl, aryl, or together represent —O— or —S—;

$R_{15}$ and $R_{16}$ each independently represents hydrogen, alkyl, aryl, or together represent —O— or —S—, provided that when $R_{13}$ and $R_{14}$ together represent —O— or —S—, $R_{15}$ and $R_{16}$ do not represent —O— or —S—;

p and q are each independently 0, 1 or 2 provided that when one of p and q is zero, the other is not zero.

As employed throughout this specification, the term "halogen" refers to fluoro, chloro, bromo and iodo, with chloro and fluoro being preferred. The term "lower", as it modifies such radical as alkyl, alkylene (as used herein "alkylene" refers to saturated divalent alkyl derived radicals), alkene, alkoxy and the like, unless otherwise stated, means straight and branched-chain radicals having up to 6 carbon atoms, e.g., methyl, ethyl, propyl, butyl, t-butyl, isopropyl, neopentyl, dimethylbutyl, propenylene, allylene (—CH$_2$—CH=CH—), ethenylene (—CH=CH—), methylene (—CH$_2$—), ethylene (—CH$_2$—CH$_2$—), propylene (—CH$_2$—CH$_2$—CH$_2$—) and the like. Methyl is the preferred lower alkyl and is especially preferred at $R_2$ and/or $R_3$ in Formula I and II. The radical

is most preferably —NH$_2$, particularly at $R_3$.

"Pyridyl" includes the 2-, 3-, and 4-isomers and their halogen- and lower alkyl-substituted analogs; "thienyl" includes the 2-, and 3-isomers and their halogen- and lower alkylsubstituted analogs; "imidazolyl" includes the 2- and 4-isomers, and their halogen-and lower alkyl substituted analogs. When the moiety "Ar" is the X'-, Y'-, Z'-substituted phenyl radical, it is preferred that the substituents be halogen which may be in the ortho, meta and/or para positions of the phenyl group. In those compounds in which the X-substituent is other then hydrogen, it may be at one or more of the 6- or 7-positions of the imidazo[1,2-b]pyridazine nucleus which are not already substituted by the "Z—T$_m$—W" group of Formula I or by the "U" group of Formula II, said latter two groups being preferably at the 8-position. When $R_4$ and $R_5$ are other than hydrogen, it is preferred that they be methyl or ethyl. "T" preferably represents methylene (—CH$_2$—) or allylene (—CH$_2$—CH=CH—) when "Z" represents —O—, or methylene when Z represents —NH—, and ethylene (—CH$_2$CH$_2$—), ethenylene (—CH=CH—) or -propenylene (—CH=CH—CH$_2$—) when "Z" represents a single bond.

"Pharmaceutically acceptable salts" includes salts wherein the acidic hydrogen in the carboxylic acid derivatives of this invention (e.g., wherein $R_2$ is COOH) is replaced with a cation (e.g., sodium) as well as salts wherein an acidic hydrogen forms an acid addition salt with an amine, e.g., the phosphate salt of 3-amino-2-methyl-8-phenylmethoxyimidazo[1,2-b]pyridazine.

Among the pharmaceutically acceptable cationic salts contemplated for this invention are salts of alkali and alkaline earth metals, e.g. sodium, potassium and calcium, also aluminum, as well as salts with an amine, such as an N-methyl glucamine salt. Suitable acids for the pharmaceutically acceptable acid addition salts include hydrochloric, sulfuric, phosphoric, nitric, acetic, propionic, maleic, ascorbic, citric and the like.

Both the cationic salts and acid addition salts are prepared via procedures well known in the art.

A preferred subgroup of compounds of Formula I are those wherein $R_2$ and $R_3$ each independently represent hydrogen, lower alkyl with 1 to 3 carbon atoms,

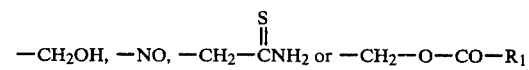

(wherein $R_1$ represents methyl, ethyl, propyl, isopropyl, t-butyl or dimethylaminomethyl) or —S(O)$_n$—CH$_3$ (wherein n is zero, one or two);

X represents hydrogen or methyl;

Z represents —O—, —NH—, —S— or a single bond;

B represents a branched or straight chain lower alkylene group;

T represents a branched or straight chain lower alkylene group, and when Z is a single bond, T also represents an ethenylene group or a propenylene group; and when Z is —O—, T also represents an allylene group; and W represents allyl or Ar, wherein Ar is selected from substituted-phenyl, phenyl, thienyl, or pyridyl groups, wherein there are one or more substituents on the phenyl group independently selected from —H, —Cl, —F, $CH_3$, -t-butyl, —$CF_3$, —$OCH_3$, —CN and —OH.

A more preferred subgroup of compounds of the preferred subgroup of Formula I are those substituted at the 8-position by "Z—$T_m$W" and W is phenyl or 3-thienyl.

Preferred compounds of Formula I are represented by the following formula:

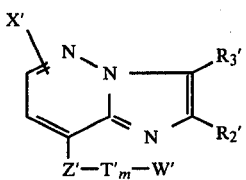

wherein $R'_2$ and $R'_3$ independently represent —$CH_2OH$, —$CH_2CN$, —NO or —$NH_2$; X' represents hydrogen; Z' represents —O—, —NH— or a single bond; $T_m'$ represents —$CH_2$—, —$CH_2CH_2$—, $CH_3\overset{|}{\underset{|}{CH}}$, —$CH_2$—$CH_2$—$CH_2$—, —CH=CH— or —CH=CH—$CH_2$—;

and W' represents Ar' wherein Ar' is phenyl, o- or p-fluorophenyl, p-chlorophenyl, 2,4,6-trimethylphenyl, 2-thienyl or 3-thienyl.

The most preferred compounds of Formula I are those substituted by "Z—$T_m$W" at the 8-position wherein: $R_2$ and $R_3$ independently represent —H, —$CH_3$, —$CH_2CN$, —$NH_2$, or —$CH_2OH$; X represents hydrogen, methyl; Z represents —O—, —NH—, or a single bond; when Z is —O— or —NH—, $T_m$ represents —$CH_2$—, and when Z represents a single bond, $T_m$ additionally represents —$CH_2CH_2$—, —CH=CH— or —CH=CH—$CH_2$—; and W represents Ar wherein Ar is phenyl or 3-thienyl.

Other preferred compounds having the substituents as defined in Formula I' can be substituted at the 6- or 7-position by Z'—$T'_m$W' although those substituted at the 8-position are more preferred.

Thus, the preferred "Z—$T_m$W" substituents of Formula I include phenylmethoxy (also called benzyloxy), phenylmethanamino, thienylmethoxy, thienylmethanamino, phenylethyl, 3-phenyl-1-propenyl, thienylethyl or 2-phenylethenyl.

Preferred compounds of Formula II include those wherein $R_2$ and $R_3$ each independently represent hydrogen, methyl,

—$CH_2OH$, —$CH_2CN$, —$CH_2OCOCH_3$,

-continued

—$CH_2$—$\overset{\overset{S}{\|}}{C}$—$NH_2$, —$NH_2$ or —NO;

X represents hydrogen;

U represents —$CH_2$—O—Ar, wherein Ar is phenyl, o- or p-fluorophenyl, p-chlorophenyl, 2,4,6-trimethylphenyl, 2-thienyl or 3-thienyl. More preferred compounds are wherein the "U" group is phenoxymethyl and the most preferred compounds are those in which "U" is at the 8-position of the imidazo[1,2-b]pyradazine nucleus.

Examples of imidazo[1,2-b]pyridazine compounds within the scope of this invention are:
1. 2,3-Dimethyl-8-phenylmethoxyimidazo[1,2-b]pyridazine;
2. 3-Amino-2-methyl-8-phenylmethoxyimidazo[1,2-b]pyridazine;
3. 2-Methyl-8-phenylmethoxyimidazo[1,2-b]pyridazine-3-acetonitrile;
4. 8-(4-Fluorophenylmethoxy)-2-methylimidazo[1,2-b]pyridazine3-thioacetamide;
5. 3-Amino-8-[2-(4-chlorophenyl)ethyl]-2-methylimidazo[1,2-]pyridazine;
6. 2-Methyl-3-nitroso-8-(2-phenylethyl)imidazo[1,2-b]pyridazine;
7. 3-Amino-2-methyl-8-(3-phenyl-1-propenyl)imidazo[1,2-b]-pyridazine;
8. 2-Methyl-8-(3-phenyl-1-propenyl)imidazo[1,2-b]pyridazine-3-acetonitrile;
9. 3-Amino-2-methyl-8-(2-phenylethenyl)imidazo[1,2-b]-pyridazine;
10. 8-(2-Fluorophenylmethoxy)-3-hydroxymethyl-2-methyl-imidazo[1,2-b]pyridazine;
11. 3-Amino-2-methyl-8-(3-thienylethyl)imidazo[1,2-b]-pyridazine;
12. 3-Acetoxymethyl-2-methyl-8-(4-fluorophenylmethoxy)-imidazo[1,2-b]pyridazine;
13. 8-Phenylmethanamino-2-methylimidazo[1,2-b]pyridazine-3-acetonitrile;
14. 2-Amino-3-methyl-8-phenylmethoxyimidazo[1,2-b]pyridazine;
15. 2-Hydroxymethyl-3-methyl-8-(2-phenylethyl)imidazo[1,2-b]-pyridazine;
16. 2,3-Diamino-8-phenylmethoxyimidazo[1,2-b]pyridazine;
17. 2-Methyl-3-methylamino-8-phenylmethoxyimidazo[1,2-b]-pyridazine;
18. 2,3-Dimethyl-8-(2-phenylethenyl)imidazo[1,2-b]pyridazine;
19. 2,3-Dimethyl-8-[2-(3-thienyl)ethenyl]imidazo[1,2-b]]-pyridazine;
20. 3-Amino-8-[2-(3-thienyl)ethenyl]-2-methylimidazo[1,2-b]-pyridazine;
21. 2-Methyl-8-(2-phenylethenyl)imidazo[1,2-b]pyridazine-3-acetonitrile.

DETAILED DESCRIPTION OF THE INVENTION

There is no single generic preparative method by which the compounds of this invention can be prepared because of the nature and positioning of the various substituents on the imidazo[1,2-b]pyridazine nucleus. Generally, the compounds can be prepared by known methods using as starting materials either known compounds or compounds which can be made by conventional means. The particular methods and sequence of reactions is dictated by the specific substituents and their positions. More than one sequence of reactions may be used for certain of the specific compounds or subgenera within the scope of this invention. Generally, the imidazo[1,2-b]pyridazine compounds of this invention can be prepared by reacting the appropriate 6-, 5- and/or 4-substituted, preferably the 4-substituted, 3-aminopyridazine with a reactive halogenated carbonyl compound, i.e., a halogenated aldehyde or ketone as shown in the following reaction Scheme I:

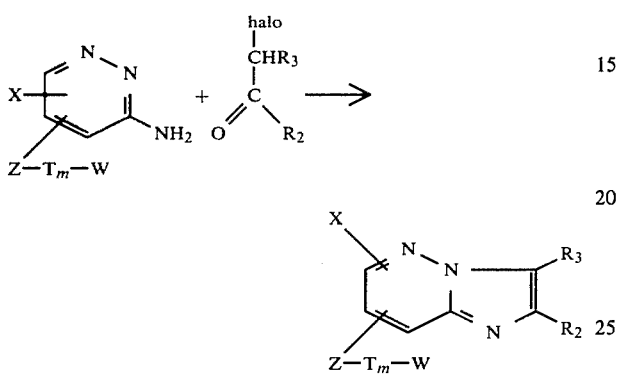

The reactants are heated together either neat or in a non-reactive anhydrous solvent under basic or neutral conditions at temperatures of from about 50° C. to 150° C.

For example, condensation of 3-amino-4-phenylmethoxypyridazine with chloroacetone gives an 8-phenylmethoxyimidazo[1,2-b]pyridazine with a methyl at the 2-position and a hydrogen as shown in the following reaction Scheme II:

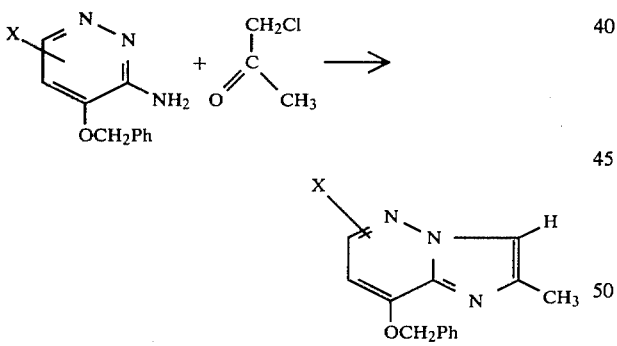

An imidazo[1,2-b]pyridazine with the 2-methyl and 3-carboethoxy substituents can be prepared by reacting a 3-amino-4-phenylmethoxypyridazine with ethyl 2-chloroacetoacetate as shown in the following reaction Scheme III:

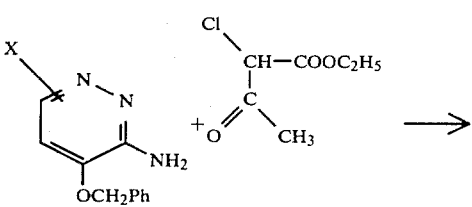

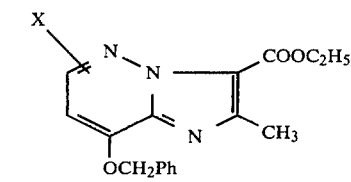

Similarly, condensation of the 3-amino-4-phenylmethoxypyridazine with 3-bromo-2-butanone gives the 2,3-dimethyl-8-phenylmethoxyimidazo[1,2-b]pyridazine as shown in the following reaction Scheme IV:

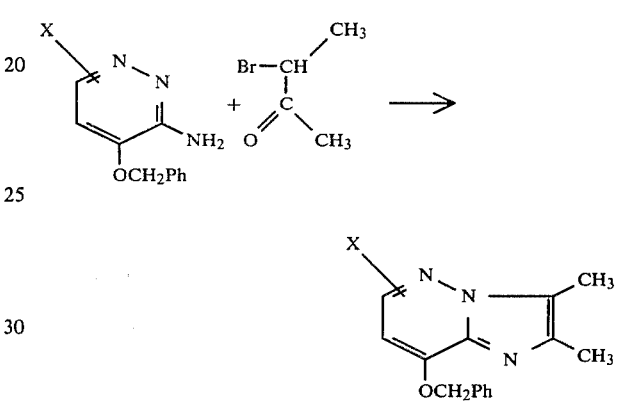

Various 3-substituted derivatives of the imidazo[1,2-b]pyridazine compounds of this inventions can be prepared from the 3-hydrogen or 3-carboethoxy derivative by conventional procedures. For example, the 3-hydrogen compound can be converted to the 3-nitro derivative using a mixture of sulfuric and nitric acids. The 3-nitro derivative can then be reduced to the corresponding 3-amino compound. Alternatively, the 3-hydrogen compound can be nitrosated to the corresponding 3-nitroso compound using sodium nitrite in hydrochloric acid solution or an alkyl nitrite, e.g. n-butyl nitrite. The 3-amino derivative can be produced by reduction of the 3-nitroso derivative, e.g., with zinc and acetic acid. The preceding reactions are illustrated in the following reaction Scheme V:

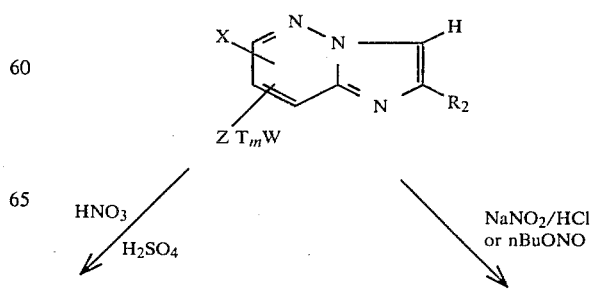

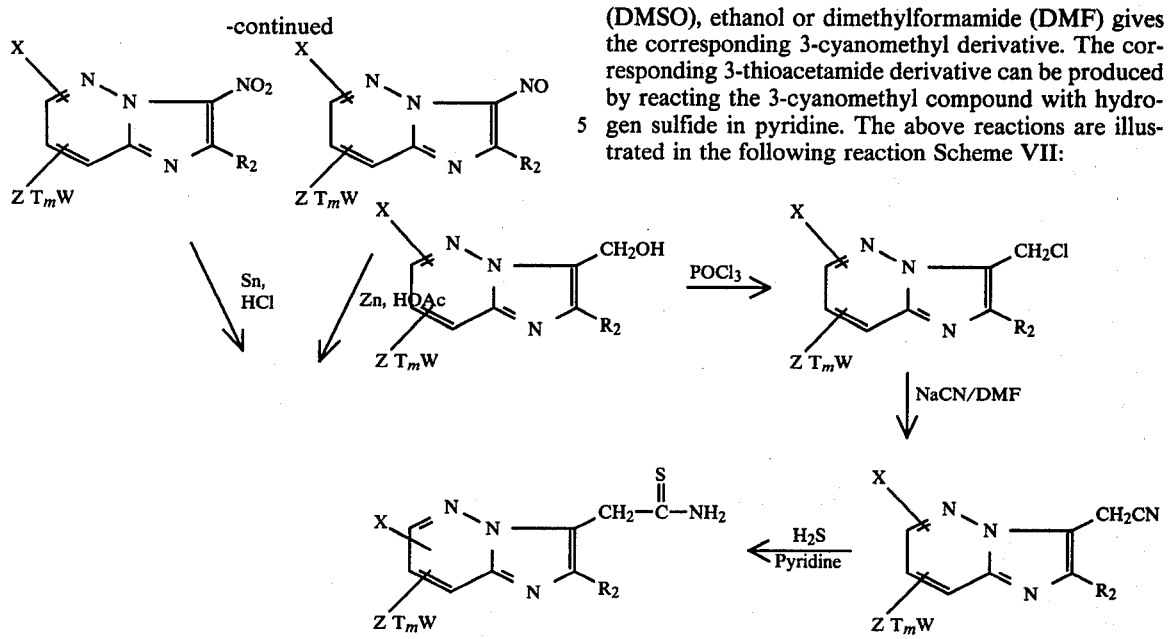

-continued

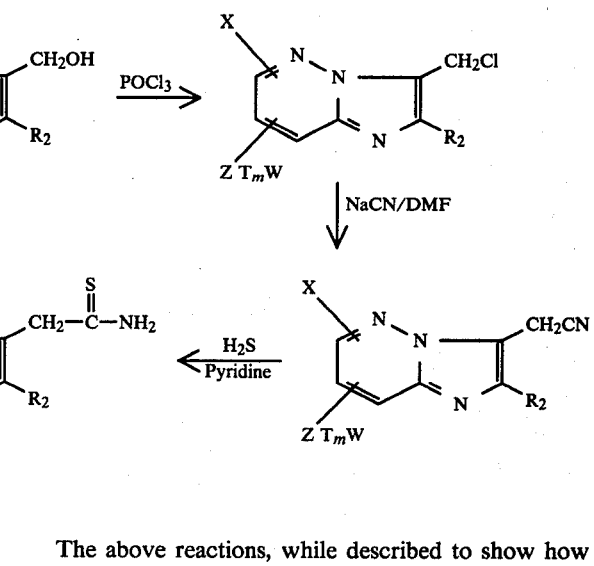

(DMSO), ethanol or dimethylformamide (DMF) gives the corresponding 3-cyanomethyl derivative. The corresponding 3-thioacetamide derivative can be produced by reacting the 3-cyanomethyl compound with hydrogen sulfide in pyridine. The above reactions are illustrated in the following reaction Scheme VII:

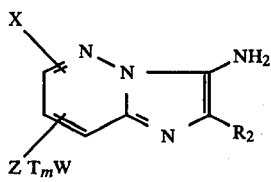

The 3-carboalkoxy compounds can be converted to the corresponding 3-hydroxymethyl derivative by reaction with lithium aluminum hydride in tetrahydrofuran (THF) as shown in the following reaction Scheme VI:

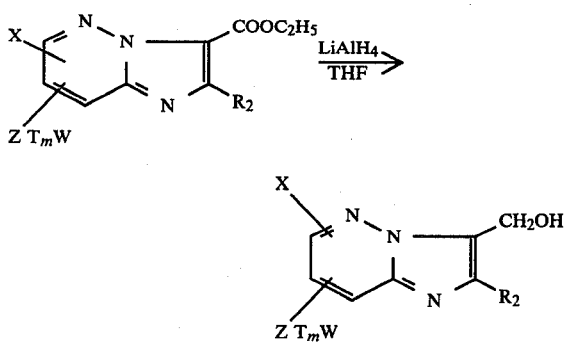

The 3-hydroxymethyl derivative can then be converted to an ester by reaction with an acid halide or an acid anhydride in an inert solvent.

In addition, the 3-hydroxymethyl derivative, upon reaction with phosphorous oxychloride is converted to the 3-chloromethyl derivative. This latter derivative, upon reaction with an alkali metal cyanide, e.g. sodium cyanide, in a suitable solvent such as dimethylsulfoxide The above reactions, while described to show how hydrogen, alkyl, carboalkoxy, nitro, nitroso, amino, hydroxymethyl, chloromethyl, cyanomethyl(acetonitrile) and thioacetamide substituents can be introduced to the 3-position of the imidazo[1,2-b]pyridazine, and how alkyl can be introduced to the 2-position are equally applicable for the introduction of other substituents at those positions by using reactants which are analogously substituted.

For example, an amino group can be introduced at the 2-position of a 3-substituted imidazo[1,2-b]pyridazine by reacting it with a mixture of nitric acid and sulfuric acid to introduce a nitro substituent at the 2-position, then reducing the nitro group to an amino group, using conventional reaction conditions.

Use of a 3-amino-4-arylalkylpyridazine to produce an imidazo[1,2-b]pyridazine results in a compound wherein "Z" of Formula I is a bond connecting "$T_m$—W" of Formula I at the 8-positon thereof.

Other transformations to the compounds of this invention wherein "Z" represents sulfur, sulfinyl and sulfonyl moieties are also effected via the use of standard methods for introducing these moieties to a pyridazine ring, e.g. after sulfur is introduced, it can be oxidized to sulfinyl or sulfonyl. Similarly, the preparations of the dihydro, tetrahydro and perhydro derivatives are effected in accordance with reduction methods which are well known for introducing hydrogen to heterocyclic and aromatic rings.

In addition to the previously described techniques, substituents can be introduced at the 8-position in 2-substituted compounds by standard alkylating procedures, e.g. reacting 8-hydroxy-2-methylimidazo[1,2-b]pyridazine with benzyl halide in the presence of a base such as sodium hydroxide and an organic solvent such as dimethylformamide(DMF) to produce 2-methyl-8-phenylalkoxyimidazo[1,2-b]pyridazine.

In general, for preparing compounds of Formula I wherein Z represents —S—, —O—, —NR$_6$—, or a single bond, the following reaction Scheme IX may be used:

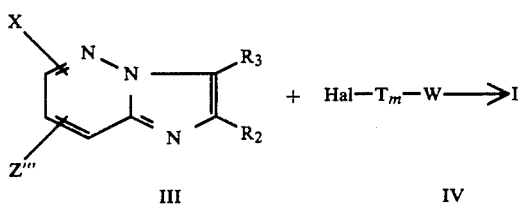

In the above Formulas III and IV, Hal represents Br, Cl or I; Z''' represents halogen (Cl,Br,I), OH or SH; W represents phenyl, thienyl, imidazolyl, furanyl or substituted phenyl; and X, $R_2$, $R_3$ and $T_m$ are as defined above.

The reactants are heated together under standard reaction conditions for the type of condensation reacton depicted, e.g., in an inert solvent in the presence of a base. When Z''' represents halogen, a copper catalyst is preferably used. When Z''' represents OH or SH, the reaction may be carried out with or without such copper catalyst.

The reaction of compounds of the above Formula III wherein Z''' is OH, with an arylcarbonyl halide, e.g. benzoyl chloride, yields a 6-, 7- or 8-benzoyloxyimidazo[1,2-b]pyradizine of Formula II, e.g., wherein p is zero, Y is O and

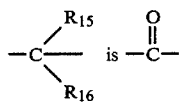

In preparing compounds of Formula II, the substituent U wherein Y is —O—, —S—, or —NR$_6$—, may be introduced by chemical modification of the corresponding imidazo[1,2-b]pyridazine having a formyl group at one of positions 6-, 7-, or 8-. Thus, for example, 8-formylimidazo[1,2-b]pyridazine having $R_2$ and $R_3$ substituents as defined hereinabove, upon reduction with sodium borohydride, is converted to the corresponding 8-hydroxymethyl derivative, an intermediate for preparing compounds of Formula II wherein Y is —O— or —S—. Etherification of the 8-hydroxymethyl intermediate, e.g., by treatment with sodium hydride followed by reaction of the resulting sodium salt with an arylalkyl halide, produces an 8-arylalkoxymethyl derivative of Formula II. Alternatively, replacement of the hydroxyl group with a leaving group, e.g. tosyl, followed by displacement thereof with an aryloxy alkali metal salt, e.g. sodium phenoxide, produces an 8-aryloxymethyl derivative of Formula II.

Similarly, replacement of the hydroxyl group with a good leaving group followed by displacement thereof with an appropriate thio reagent, e.g. an alkali metal salt of an arylalkylthiol or an arylthiol, produces compounds of Formula II wherein Y is sulfur, e.g. an 8-arylalkylthiomethyl- or an 8-arylthiomethyl-derivative, respectively.

An imidazo[1,2-b]pyridazine having a formyl group at one of positions 6-, 7-, or 8- is also a useful intermediate in introducing substituents of Formula II wherein Y is nitrogen. Thus, for example, reaction of 8-formylimidazo[1,2-b]pyridazine having $R_2$ and $R_3$ substituents as defined hereinabove with an arylamine or an arylalkylamine, followed by reduction of the resulting imines, products 8-arylaminomethyl and 8-arylalkylaminomethyl-derivatives or Formula II. Treatment of the foregoing secondary amine derivatives with a base followed by reaction with a hydrocarbon halide yields the corresponding tertiary amine derivatives of Formula II, i.e. compounds wherein Y is —NR$_6$— with R$_6$ being other than hydrogen.

Compounds of this invention having an olefinic functionality at positions 6-, 7-, or 8-, i.e. compounds of Formula I wherein Z is a bond and T is an α(β) or β(γ)-unsaturated lower alkylene, are derived from the corresponding formylimidazo[1,2-b]pyridazines having $R_2$ and $R_3$ substituents as defined above, upon reaction thereof under Wittig conditions or modifications thereof.

The starting compounds in the above reaction Scheme IX are either known or may be obtained according to standard procedures.

Compounds of Formula I wherein Z represents —SO— or —SO$_2$— may be obtained by oxidizing the corresponding compound wherein Z represents —S—, according to procedures well known in the art.

Numerous standard reactions may be applied for transferring one type of substituent $R_2$ and/or $R_3$ into another type. Thus, for example, for preparing compounds of Formula I wherein $R_3$ represents the group BCN, the following processes may be applied:

1. Subject a compound of Formula I wherein $R_2$, X, T, Z and Ar are as defined for Formula I and $R_3$ represents either BCONH$_2$ or

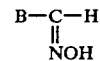

to dehydration by treating a starting compound with a suitable dehydrating agent in an inert solvent. Preferred dehydrating agents are (CF$_3$CO)$_2$O (in pyridine), SeO$_2$, POCl$_3$, and the like. The starting compounds may be obtained according to standard procedures.

2. Treat a compound of Formula I wherein $R_2$, X, T, Z and Ar are as defined for Formula I and $R_3$ represents the group

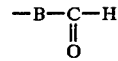

with a suitable reagent, e.g. Tosyl—CH$_2$—NC in the presence of potassium-t-butoxide whereby the formyl function is replaced by CH$_2$CN.

3. Treat a compound of Formula I wherein $R_2$, X, T, Z and Ar are as defined for Formula I and $R_3$ represents the group —B—COOR with a suitable reagent, e.g. dimethylaluminumamide, resulting in a compound where $R_3$ is —BCN.

4. Treat a compound of Formula I wherein $R_2$, X, T, Z and Ar are as defined for Formula I and $R_3$ represents the group

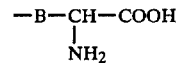

with NaOCl under standard conditions.

5. Subject a compound of Formula I wherein $R_2$, X, T, Z and Ar are as defined for Formula I and $R_3$ represents a group B—CH$_2$NO$_2$ to a reductive dehydration, e.g., with PCl$_3$ and the like in pyridine to give the desired nitrile. [See J. Org. Chem. 42, 3956 (1977)].

6. React a compound of Formula I wherein $R_2$, X, T, Z and Ar are as defined for Formula I and $R_3$ represents H with a compound of the formula Hal—B—CN wherein Hal is chlorine or bromine, in the presence of a Lewis acid, e.g. aluminum chloride, zinc chloride, boron chloride and the like, or a phase transfer catalyst.

7. Subject a compound of Formula I wherein $R_2$, X, T, Z and Ar are as defined for Formula I and $R_3$ represents the group —CH—CN to a reduction, preferably with Raney-nickel whereby the —SCH$_3$ group is replaced by a hydrogen atom. The starting compound may be obtained by reacting a compound of Formula I wherein $R_3$ represents hydrogen with CH$_3$—S—CH(Cl)CN by means of a Friedel Crafts catalyst, e.g. SnCl$_4$, TiCl$_4$, AlCl$_3$, and the like.

In addition to modifying various $R_3$ groups into —B—CN groups as described in the above reactions, other transformations may be carried out, e.g. as indicated in the following tables:

TABLE I

| STARTING $R_3$ | CHEMICAL REACTION | RESULTING $R_3$ |
|---|---|---|
| —COOC$_2$H$_5$ | reduction (LiAlH$_4$) | —CH$_2$OH |
| —CH$_2$CN | reaction with alkylhalide, base | alkyl<br>$\|$<br>—CH—CN |
| —CN | reduction with LiAlH$_4$ | —CH$_2$NH$_2$ |
| —CH$_2$NH$_2$ | 1. reaction with methyliodide<br>2. followed by reaction with metal cyanide | —CH$_2$CN |
| —CN | saponification | —COOH |
| —BOH | reaction with NaH and ClCON(CH$_3$)$_2$ | —BOCON(CH$_3$)$_2$ |
| —BCN | treatment with NaOH | —BCONH$_2$ |
| —BCN | treatment with H$_2$S | —BCSNH$_2$ |
| —BOH | treatment with SOCl$_2$ | —BCl |
| —BX″<br>(X″ = leaving group, e.g. halogen) | treatment with NO$_2^\ominus$ | —BNO$_2$ |
| —BX″<br>X″ = leaving group, e.g. halogen | reaction with CH$_3$NO$_2$, base | —BCH$_2$NO$_2$ |
| —CHO | 1. reaction with base, CH$_3$NO$_2$ resulting in CH=CHNO$_2$<br>2. treatment with NaBH$_4$ | —CH$_2$CH$_2$NO$_2$ |
| H | nitration (HNO$_3$/Acetic Acid) | —NO$_2$ |
| H | nitrosation | —NO |
| $-\!\!\overset{O}{\underset{}{\|}}\!\!-\!\!N\!\!-\!\!(O)_m$<br>(n = 0,1) | reduction | —NH$_2$ |
| —NH$_2$ | 1. diazotization<br>2. followed by reaction with an alkali metal thiocyanate | —SCN |
| H | halogenation | —Cl<br>—Br |
| H | acylation via acid chloride or acid anhydride | —COCH=CH$_2$<br>—COC≡CH<br>—COCOOR<br>(R = H, alkyl) |
| —COCOOR<br>(R = H, alkyl) | reduction (NaBH$_4$) | —CHOHCOOR |

TABLE I-continued

| STARTING $R_3$ | CHEMICAL REACTION | RESULTING $R_3$ |
|---|---|---|
| —COR<br>(R = H, alkyl) | treatment with hydrogen cyanide | OH<br>$\|$<br>—C—CN<br>$\|$<br>R |
| OH<br>$\|$<br>—C—CN<br>$\|$<br>R<br>(R = H, alkyl) | esterification | OCOR$^1$<br>$\|$<br>—C—CN<br>$\|$<br>R<br>R$^1$ = hydrocarbon |
| OH<br>$\|$<br>—C—CN<br>$\|$<br>R<br>(R = H, alkyl) | etherification | OR$^1$<br>$\|$<br>—C—CN<br>$\|$<br>R<br>(R$^1$ = hydrocarbon) |
| —CH$_2$OH | 1. (a) Phosphorylation<br>(b) or sulfonylation<br>2. followed by esterification or treatment with an alkali metal base | (a) —CH$_2$—O—$\overset{O}{\underset{\|}{P}}$—OR<br>$\|$<br>OR<br>R = H, alkali metal or alkyl<br>(b) —CH$_2$—O$\overset{O}{\underset{\|}{S}}$—OR<br>$\|$<br>O |
| —CH$_2$OH | alkylation with NaH and ClCH$_2$SCH$_3$ | —CH$_2$OCH$_2$SCH$_3$ |
| —CH$_2$OH | alkylation with NaH and ClCH$_2$SC$_6$H$_5$/NaI | —CH$_2$OCH$_2$SC$_6$H$_5$ |
| —CH$_2$OH | alkylation with NaH and R—$\overset{O}{\underset{\|}{C}}$—XCH$_2$Cl/NaI<br>(X = O, S, NR;<br>R = H, CH$_3$) | —CH$_2$OCH$_2$XCOR |

Equally the various possibilities of $R_2$ may, where appropriate, be transferred into other $R_2$-substituents by reactions such as those outlined for $R_3$ in the processes described above. Also, the following are other transformations which may be carried out at the two position to modify the $R_2$ function; which transformations may also be carried out, where appropriate, to modify the $R_3$ function at the three-position.

TABLE II

| STARTING $R_2$ | CHEMICAL REACTION | RESULTING $R_2$ |
|---|---|---|
| CH$_3$<br>$\|$<br>—CH—COOC$_2$H$_5$ | alkylation with NaH and CH$_3$I | —C—(CH$_3$)$_2$<br>/<br>COOC$_2$H$_5$ |
| —(CH$_2$)$_n$COOR<br>R = H, alkyl<br>n = 0, 1 | Reduction | —(CH$_2$)$_n$CHO |
| —(CH$_2$)$_n$COOH | organometallic reagent (e.g. alkyl lithium) | —(CH$_2$)$_n$—$\overset{O}{\underset{\|}{C}}$—R<br>(R = alkyl) |
| —(CH$_2$)$_n$CHO<br>(n = 0, 1) | Wittig process | —(CH$_2$)$_n$CH=CH$_2$ |
| —(CH$_2$)$_n$—COR<br>(n = 0, 1;<br>R = alkyl) | Wittig process | —(CH$_2$)$_n$CR=CH$_2$ |
| —(CH$_2$)$_n$CH=CH$_2$<br>(n = 0, 1) | halogen addition and elimination | —(CH$_2$)$_n$CR=CH |

TABLE II-continued

| STARTING R$_2$ | CHEMICAL REACTION | RESULTING R$_2$ |
|---|---|---|
| R<br>$\|$<br>—CHOH<br>(R = H, alkyl) | 1. replacement of OH with leaving group (e.g. tosyl)<br>2. nucleophilic displacement with LiC≡CH | —CHRC≡CH |
| —CHR—C≡CH<br>(R = H, alkyl) | isomerization (acid or base) | R<br>$\backslash$<br>—C=C=CH$_2$ |
| —OH<br>—OH<br>—SH | reaction with P$_2$S$_5$<br>etherification<br>etherification | —SH<br>—OR<br>—SR<br>(R = alkyl) |
| —NHCOOR<br>(R = H, alkyl) | hydrolysis | —NH$_2$ |

The sequence of certain reactions may be altered, thus, for example, one may, in accordance with methods described herein, first prepare a compound of Formula III shown hereinabove, make the above described rearrangements within the groups R$_2$ and R$_3$ and then complete the molecule by carrying out reaction Scheme IX described above.

The imidazo[1,2-b]pyridazine compounds of this invention are useful in the treatment of peptic ulcers. They display chemotherapeutic activity which enables them to relieve the symptoms of peptic ulcer disease, including stress ulceration, and promote healing of gastric and/or duodenal ulcers. The antiulcer activity of the compounds of this invention is identified by tests which measure their cytoprotective effect (also referred to as mucoprotective effect) and antisecretory effect in rats. The compounds are also useful as conjunctive therapeutic agents for coadministration with such anti-inflammatory/analgesic agents as aspirin, indomethacin, phenylbutazone, ibuprofen, naproxen, tolmetin and other agents having the untoward side effect of contributing irritation and damage to the gastrointestinal tract.

The compounds of this invention are evaluated for their activity characteristics by standard biological testing procedures.

In the testing procedures they are evaluated on an absolute basis and on a comparative basis with compounds known to possess the activity useful for the treatment and/or prevention of peptic ulcer disease and drug induced gastric ulceration. Such tests include testing for antisecretory effects in rats with pyloric ligation techniques. The test compounds are administered either intraperitoneally or orally in appropriate and well-defined and well-known vehicles.

In cytoprotective tests in rats in which ethanol is employed to induce gastrointestinal damage, the compounds of this invention are found to be effective for the oral treatment of the ulcerative disease states mentioned herein.

Orally, the compounds are effective at doses of about 0.5–50 mg/kg of body weight per day. Preferably the total dosages are administered in 2–4 divided doses per day.

When administered parenterally, e.g. intravenously, the compounds are administered at a dosage range of about 0.01 to 10 mg/kg body weight in single or multiple daily doses. Of course, the dose will be regulated according to the judgment of the attending clinician depending on factors such as the degree and severity of the disease state and age and general condition of the patient being treated. The usual dosage range for the preferred compounds of this invention is an oral dose of about 75 to 1600 mg/day, preferably 600 to 800 mg/day, in 2 to 4 divided doses. This dosage regimen achieves relief of the symptoms of peptic ulcer disease and promotes the healing of gastric and/or duodenal ulcers.

To treat peptic ulcer disease, gastric and duodenal ulcers, and prevent and treat drug-induced gastric ulceration, the active compounds of this invention can be administered in unit dosage forms such as tablets, capsules, pills, powders, granules, sterile parenteral solutions or suspensions, suppositories mechanical delivery devices, e.g. transdermal, and the like. Such dosage forms are prepared according to standard techniques well-known in the art.

The following example illustrates the preparation of compounds and compositions of this invention. All temperatures are in degrees Celsius.

EXAMPLE 1

A mixture of (0.01 mole) 3-amino-6-methyl-4-phenyl-methoxypyridazine, [prepared following the methodology of Becket, et al. J. Pract. Chem., 311, 285(1969) and references cited therein], and (0.012 mole) 2-bromo-3-butanone in methanol is heated for 24 hours in a bath maintained at 100°. The mixture is cooled to room temperature and partitioned between aqueous sodium bicarbonate and methylene chloride. The layers are separated and the aqueous phase extracted with methylene chloride. The organic extracts are combined and dried over anhydrous sodium sulfate. The solvent is removed under reduced pressure to give 6-methyl-8-phenylmethoxy-2,3-dimethylimidazo[1,2-b]pyridazine.

Following the procedures of Example I using appropriate reagents, the following compounds can be prepared;

2,3-dimethyl-8-phenylmethoxyimidazo[1,2-b]-pyridazine;

8-phenylmethoxy-2-methyl-3-aminoimidazo[1,2-b]-pyridazine.

The following formulations exemplify some of the dosage forms in which the compounds of this invention may be employed. In each, the active ingredient is designated by the term "Drug" which is meant to indicate one of the following compounds:

8-phenylmethoxy-2-methylimidazo[1,2-b]-pyridazine-3 acetonitrile;

2,3-dimethyl-8-phenylmethoxyimidazo[1,2-b]-pyridazine; and 8-phenylmethoxy-2-methyl-3-aminoimidazo[1,2-b]-pyridazine.

It is contemplated, however, that each of these exemplar compounds may be replaced by equally effective quantities of other compounds within the scope of Formulas I and II. All temperatures are in degrees Celsius.

Formulation 1

Tablets

| No. | Ingredient | mg/tab | mg/tab |
|---|---|---|---|
| 1 | Drug | 25.0 | 400.0 |
| 2 | Lactose, impalpable powder, USP | 114.0 | 241.5 |
| 3 | Corn Starch, USP | 25.0 | 50.0 |
| 4 | Corn Starch as 5% paste in distilled water | 10.0 | 35.0 |

Formulation 1-continued

Tablets

| No. | Ingredient | mg/tab | mg/tab |
|---|---|---|---|
| 5 | Corn Starch, USP | 25.0 | 50.0 |
| 6 | Magnesium Stearate, USP | 1.0 | 3.5 |
|   |   | 200.0 | 780.0 |

Method of Manufacture

Mix items Nos. 1, 2 and 3 in a suitable blender for 5 to 15 minutes. Pass through a fine screen (#40) if necessary. Reblend for 5 to 10 minutes and granulate with item No. 4. Pass the damp granulated mass through a coarse sieve (#6) using a suitable mill. Dry the damp granules at 40° to 50° overnight. Mill the dried granules using a No. 20 screen. Add item No. 5 and blend for 5 to 10 minutes. Add item No. 6 and blend further for 3 to 5 minutes. Compress the tablet mixture into tablets of an appropriate size and weight using a suitable tableting machine.

Formulation 2

Capsules

| No. | Ingredient | mg/tab | mg/tab |
|---|---|---|---|
| 1 | Drug | 25.0 | 400.0 |
| 2 | Lactose, impalpable powder, USP | 144.0 | 191.5 |
| 3 | Corn Starch, USP | 30.0 | 105.0 |
| 4 | Magnesium Stearate, USP | 1.0 | 3.5 |
|   |   | 200.0 | 700.0 |

Method of Manufacture

Mix items Nos. 1, 2 and 3 in a suitable blender for 5 to 10 minutes. Pass through a fine screen (#40) if necessary. Reblend for 5 to 10 minutes, add item No. 4 and mix further for 3 to 50 minutes. Using a suitable machine, encapsulate the mixture into a two-piece hard gelatin capsule of appropriate size.

Formulation 3

Suspensions

| Ingredients | Formula A (mg/ml) | Formula B (mg/ml) |
|---|---|---|
| Drug | 5.0 | 80.0 |
| Sucrose | 600.0 | 600.0 |
| Benzyl alcohol | 10.0 | 10.0 |
| Methylcellulose (15 cps) | 4.0 | 4.0 |
| Polysorbate 80 | 5.0 | 5.0 |
| Vanillin | 0.2 | 0.2 |
| Purified Water q.s. | 1.0 ml | 1.0 ml |

Method of Manufacture

1. Charge approximately 40% of the final volume of purified water in a stainless steel tank. Heat to boiling. Agitate using an appropriate stirrer. Agitation should continue throughout procedure.
2. Add sucrose until it is dissolved.
3. Slowly add methylcellulose until it is well dispersed.
4. Start cooling the mixture to room temperature.
5. Add polysorbate, benzyl alcohol and vanillin until all ingredients are well dispersed.
6. Add the Drug until a uniform dispersion is formed.
7. Dilute the suspension to final volume with purified water at 25°.

Formulation 4

Parenteral

|   | mg/ml |
|---|---|
| Drug | 25.0 |
| Methylparaben | 1.3 |
| Propylparaben | 0.2 |
| Sodium bisulfite | 3.2 |
| Disodium edetate | 0.2 |
| Sodium sulfate | 2.6 |
| Water for injection q.s. | 1.0 ml |

Method for Manufacture

1. Dissolve parabens in a portion (approximately 85% of the final volume) of the water for injection at 65°–70°.
2. Cool to 25°–35°. Charge and dissolve sodium bisulfite, disodium edetate and sodium sulfate.
3. Charge and dissolve the Drug.
4. Bring the solution to the final volume by adding water for injection.
5. Filter the solution through a 0.22 micron membrane and fill into appropriate containers.
6. Terminally sterilize the units by autoclaving.

Formulation 5

Injectable Suspension

|   | mg/ml |
|---|---|
| Drug (Sterile) | 50.0 |
| Benzyl alcohol | 9.0 |
| Methylparaben | 1.8 |
| Propylparaben | 0.2 |
| Sodium carboxymethylcellulose | 5.0 |
| Polyethylene Glycol 4000 | 10.0 |
| Povidone | 5.0 |
| Sodium Citrate | 15.0 |
| Disodium edetate | 0.1 |
| Water for injection q.s. | 1.0 ml |

Method of Preparation

1. Dissolve parabens in a portion of water for injection at 65°–70°.
2. Cool to 25°–35°. Charge and dissolve benzyl alcohol, sodium citrate, disodium edetate, PEG 4000, povidone and sodium carboxymethylcellulose.
3. Filter the solution and sterilize by autoclaving.
4. Make a slurry of the sterile Drug and pass it through a colloid mill.
5. Mix it well with solution from Step 3 and pass it through the mill.
6. Bring the suspension to the final volume/weight and fill into sterile containers.

Formulation 6

Suppositories

| A. Formula | mg/supp |
|---|---|
| Drug | 5.0 |
| Cocoa butter | 1995.0 |
|   | 2000.0 mg. (2.0 g.) |

Procedure

1. Melt cocoa butter to about 32°–35°.
2. Blend Drug into cocoa butter until well dispersed.
3. Pour into teflon-coated mold and congeal in refrigerator. Keep in refrigerator for an appropriate length of time.

4. Remove suppositories from mold.

| B. Formula | mg/supp |
|---|---|
| Drug | 100.0 |
| PEG 1000 | 1824.0 |
| PEG 4000 | 76.0 |
| | 2000.0 m.g. |
| | (2.0 g.) |

Procedure

1. Melt PEG 1000 and PEG 4000 in one container to 50°.
2. Add Drug to mixture. Blend until well dispersed.
3. Pour into mold and congeal in refrigerator. Keep in refrigerator for an appropriate length of time.
4. Remove suppositories from mold.

Since all the compounds within the large class of compounds encompassed by this invention are not equally therapeutically potent, certain subgroups and certain specific compounds have been found to be preferred for their therapeutic utility. Preferred are those compounds wherein the imidazo[1,2-b]pyridazine nucleus is substituted in the 8-position through an oxygen or nitrogen atom. Another preferred group is where the "Ar" substituent represent phenyl or 3-thienyl. Also, another preferred group contains the "Ar" moiety attached to the 8-position of the imidazo[1,2-b]pyridazine nucleus through a methoxy, ethoxy, methylamino or ethylamino linkage i.e., wherein T represent methylene or ethylene or directly through an ethylene, ethylenylene or propenylene linkage, i.e., where Z is a bond and T is ethylene, ethenylene or propenylene. Still, another preferred group consists of those compounds containing a cyanomethyl, an amino or an alkyl substituent, particularly methyl, at the 2-position and methyl or amino at the 3-position. Yet, another preferred group consists of those compounds having a hydroxyalkyl, preferably hydroxymethyl, at the 2-position or the 3-position. Preferred specific compounds include those imidazo[1,2-b]-pyridazine of Formulas I and II having the following substituents:

| $R_2$ | $R_3$ | X | Z | T | (m) | AR |
|---|---|---|---|---|---|---|
| CH$_3$ | CH$_2$CN | H | O | CH$_2$ | 1 | phenyl |
| CH$_2$OH | CH$_2$CN | H | O | CH$_2$ | 1 | phenyl |
| CH$_3$ | CH$_2$CN | H | O | CH$_2$ | 1 | thienyl |
| CH$_3$ | NH$_2$ | H | O | CH$_2$ | 1 | phenyl |
| CH$_3$ | CH$_2$OH | H | O | CH$_2$ | 1 | phenyl |
| CH$_3$ | CH$_2$CN | H | NH | CH$_2$ | 1 | phenyl |
| CH$_3$ | CH$_2$CN | H | (Bond) | CH$_2$ | 2 | phenyl |
| CH$_3$ | CH$_3$ | H | O | CH$_2$ | 1 | phenyl |
| CH$_3$ | NH$_2$ | H | O | CH$_2$ | 1 | thienyl |
| CH$_3$ | NH$_2$ | H | (Bond) | CH$_2$ | 2 | phenyl |
| CH$_3$ | NH$_2$ | H | NH | CH$_2$ | 1 | phenyl |
| CH$_2$CN | CH$_3$ | H | O | CH$_2$ | 1 | phenyl |
| CH$_2$CN | CH$_3$ | H | NH | CH$_2$ | 1 | thienyl |
| CH$_2$CN | CH$_3$ | H | (Bond) | CH$_2$ | 2 | thienyl |
| CH$_2$CN | CH$_3$ | H | (Bond) | CH$_2$ | 3 | thienyl |
| CH$_2$CN | CH$_3$ | H | (Bond) | CH$_2$ | 3 | phenyl |
| CH$_3$ | NH$_2$ | H | (Bond) | —CH=CH—CH$_2$— | 1 | phenyl |
| CH$_3$ | NH$_2$ | H | (Bond) | —CH=CH— | 1 | phenyl |
| CH$_3$ | NH$_2$ | H | (Bond) | —CH=CH— | 1 | thienyl |
| CH$_3$ | CH$_3$ | H | (Bond) | —CH=CH— | 1 | phenyl |
| CH$_3$ | CH$_3$ | H | (Bond) | —CH=CH— | 1 | thienyl |
| CH$_3$ | CH$_2$CN | H | (Bond) | —CH=CH— | 1 | phenyl |
| CH$_3$ | CH$_2$CN | H | (Bond) | —CH=CH— | 1 | thienyl |
| CH$_3$ | CH$_3$ | H | (Bond) | —CH=CHCH$_2$— | 1 | phenyl |
| CH$_3$ | CH$_2$CN | H | (Bond) | —CH=CHCH$_2$— | 1 | phenyl |

We claim:

1. A compound represented by the formula:

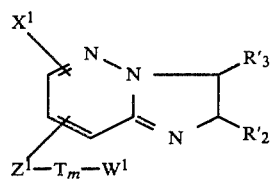

and pharmaceutically acceptable salts thereof, wherein $R'_2$ and $R'_3$ independently represent methyl, cyanomethyl or amino; $X'$ represents hydrogen or methyl; and $Z'$—$T'_m$—$W'$ represents phenylmethoxy, phenylmethanamino, phenylethyl, 2-phenylethenyl or 3-phenyl-1-propenyl.

2. The compound of claim 1 wherein $R'_2$ and $R'_3$ are each methyl; and $Z'$—$T'_m$—$W'$ is phenylethenyl, i.e. 2,3-dimethyl-8-phenylenthenylimidazo[1,2-b]pyridazine.

3. The compound of claim 1 wherein $R'_2$ is methyl, $R'_3$ is cyanomethyl and $Z'$—$T'_m$—$W'$ is phenylmethoxy, i.e. 2-methyl-8-phenylmethoxyimidazo[1,2-b]pyridazine-3-acetonitrile.

4. The compound of claim 1 wherein $R'_2$ is methyl, $R'_3$ is amino and $Z'$—$T'_m$—$W'$ is phenylmethoxy, i.e. 8-phenylmethoxy-2-methyl-3-aminoimidazo[1,2-b]pyridazine.

5. A method for the treatment of the symptoms of peptic ulcer disease in mammals, which comprises administering to a mammal having peptic ulcer disease a therapeutically effective amount of a compound of claim 1.

6. A method for the treatment of gastric ulcers in mammals which comprises administering to a mammal having gastric ulcers a therapeutically effective amount of a compound of claim 1.

7. A method for the treatment of duodenal ulcers in mammals which comprises administering to a mammal having duodenal ulcers a therapeutically effective amount of a compound of claim 1.

8. A method for inhibiting gastrointestinal irritation and damage in mammals due to administration of drugs which induce gastrointestinal irritation and damage which comprises administering a therapeutically effective amount of a compound of claim 1 during the term said gastro-intestinal irritating and damaging drug is administered for its therapeutic effect.

9. A method for the treatment of gastrointestinal damage due to stress which comprises administering to a mammal suffering from such damage a therapeutically effective amount of a compound of claim 1.

10. A method of claim 10 which comprises administering to a mammal having peptic ulcer disease, a therapeutically effective amount of a compound of claims 2, 3 or 4.

11. A pharmaceutical compound for use in the treatment of ulcers which comprises a compound of claim 1 in a therapeutically effective amount sufficient to alleviate the symptoms of peptic ulcer disease together with a pharmaceutically acceptable carrier.

12. A pharmaceutical compound of claim 11 which comprises a therapeutically effective amount of a compound of claim 2 together with a pharmaceutically acceptable carrier.

13. A pharmaceutical compound of claim 11 which comprises a therapeutically effective amount of a compound of claim 3 together with a pharmaceutically acceptable carrier.

14. A pharmaceutical formulation of claim 11 which comprises a therapeutically effective amount of a compound of claim 4 together with a pharmaceutically acceptable carrier.

15. A pharmaceutical composition of claims 11, 12 or 13 suitable for oral administration.

* * * * *